US009623180B2

(12) United States Patent
Iio et al.

(10) Patent No.: US 9,623,180 B2
(45) Date of Patent: Apr. 18, 2017

(54) PHARMACEUTICAL INJECTION SYSTEM

(75) Inventors: Toshiaki Iio, Ehime (JP); Yukihiro Takabatake, Ehime (JP); Seiji Kikuchi, Ehime (JP); Tsuguhiro Kondoh, Ehime (JP); Shinsuke Hata, Ehime (JP); Takashi Hanada, Hyogo (JP)

(73) Assignees: PANASONIC HEALTHCARE CO., LTD., Toon-Shi (JP); JCR PHARMACEUTICALS CO., LTD., Ashiya-Shi (JP)

( * ) Notice: Subject to any disclaimer, the term of this patent is extended or adjusted under 35 U.S.C. 154(b) by 447 days.

(21) Appl. No.: 14/343,548

(22) PCT Filed: Sep. 10, 2012

(86) PCT No.: PCT/JP2012/005709
§ 371 (c)(1),
(2), (4) Date: Mar. 7, 2014

(87) PCT Pub. No.: WO2013/038638
PCT Pub. Date: Mar. 21, 2013

(65) Prior Publication Data
US 2014/0228766 A1 Aug. 14, 2014

(30) Foreign Application Priority Data
Sep. 12, 2011 (JP) .................. 2011-198100

(51) Int. Cl.
*A61M 5/20* (2006.01)
*A61M 5/00* (2006.01)
*H02J 7/00* (2006.01)

(52) U.S. Cl.
CPC .............. *A61M 5/20* (2013.01); *A61M 5/00* (2013.01); *H02J 7/0068* (2013.01);
(Continued)

(58) Field of Classification Search
CPC ...... A61M 5/20; A61M 5/00; A61M 2205/18; A61M 2005/2006; A61M 2205/123; A61M 2205/14; A61M 2205/8256; H02J 7/0068
See application file for complete search history.

(56) References Cited

U.S. PATENT DOCUMENTS 5,322,511 A * 6/1994 Armbruster ............. A61M 5/20
604/152
6,159,161 A * 12/2000 Hodosh .................. A61M 5/20
600/561
(Continued)

FOREIGN PATENT DOCUMENTS

JP    H11513586 A    11/1999
JP    2006-034719 A   2/2006
(Continued)

OTHER PUBLICATIONS

Office Action for Application No. JP 2013-533487 dated Jun. 2, 2015.
(Continued)

*Primary Examiner* — Kevin C Sirmons
*Assistant Examiner* — Amber Stiles
(74) *Attorney, Agent, or Firm* — Pearne & Gordon LLP

(57) ABSTRACT

This pharmaceutical injection system is provided with a pharmaceutical injection device, a charging device, a detector, and an alarm section. The pharmaceutical injection device has a main body case and a pharmaceutical syringe mounting portion provided within the main body case and to which a pharmaceutical syringe is removably mounted. The pharmaceutical injection device is placed in the charging device, and the charging device has a charger for charging the pharmaceutical injection device. The detector is provided to the pharmaceutical injection device and/or the charging device and detects whether or not the pharmaceu-
(Continued)

tical syringe has been mounted to the pharmaceutical syringe mounting portion. The alarm section is connected to the detector and emits an alarm when it is detected that the pharmaceutical syringe has been mounted onto the pharmaceutical syringe mounting portion.

5 Claims, 7 Drawing Sheets

(52) U.S. Cl.
CPC ............... *A61M 2005/2006* (2013.01); *A61M 2205/123* (2013.01); *A61M 2205/14* (2013.01); *A61M 2205/18* (2013.01); *A61M 2205/8256* (2013.01)

(56) References Cited

U.S. PATENT DOCUMENTS

| | | | |
|---|---|---|---|
| 6,544,200 B1* | 4/2003 | Smith | A61B 5/1117 340/573.1 |
| 7,749,186 B2 | 7/2010 | Kohlbrenner et al. | |
| 8,211,067 B2 | 7/2012 | Nemoto | |
| 8,398,602 B2 | 3/2013 | Iio et al. | |
| 8,556,847 B2 | 10/2013 | Kohlbrenner et al. | |
| 8,771,233 B2 | 7/2014 | Watanabe et al. | |
| 2004/0210199 A1 | 10/2004 | Atterbury et al. | |
| 2005/0171476 A1 | 8/2005 | Judson et al. | |
| 2005/0197650 A1 | 9/2005 | Sugimoto et al. | |
| 2006/0151049 A1* | 7/2006 | Nemoto | A61M 5/14546 141/27 |
| 2007/0021715 A1 | 1/2007 | Kohlbrenner et al. | |
| 2007/0142777 A1 | 6/2007 | Klein | |
| 2009/0131756 A1 | 5/2009 | Nemoto | |
| 2009/0299328 A1* | 12/2009 | Mudd | A61M 5/20 604/506 |
| 2010/0238038 A1 | 9/2010 | Kohlbrenner et al. | |
| 2010/0262078 A1 | 10/2010 | Blomquist | |
| 2011/0144574 A1* | 6/2011 | Kamen | A61M 5/14224 604/67 |
| 2011/0218502 A1 | 9/2011 | Iio et al. | |
| 2011/0238017 A1 | 9/2011 | Watanabe et al. | |
| 2011/0257602 A1 | 10/2011 | Watanabe et al. | |
| 2011/0313349 A1 | 12/2011 | Krulevitch et al. | |
| 2011/0313350 A1 | 12/2011 | Krulevitch et al. | |
| 2011/0313395 A1 | 12/2011 | Krulevitch et al. | |
| 2012/0004637 A1 | 1/2012 | Krulevitch et al. | |
| 2012/0323176 A1 | 12/2012 | Watanabe et al. | |
| 2013/0175192 A1 | 7/2013 | Iio et al. | |

FOREIGN PATENT DOCUMENTS

| | | |
|---|---|---|
| WO | 97/14459 A1 | 4/1997 |
| WO | 2006/059597 A1 | 6/2006 |
| WO | 2010/0055608 A1 | 5/2010 |
| WO | 2010/070799 A1 | 6/2010 |
| WO | 2010/073452 A1 | 7/2010 |
| WO | 2010/098931 A1 | 9/2010 |
| WO | 2011/108225 A1 | 9/2011 |

OTHER PUBLICATIONS

Extended European Search Report for Application No. 12831697.3-1662/2756855 PCT/JP2012005712 dated Dec. 8, 2014.
International Search Report for PCT/JP2012/005709 dated Oct. 23, 2012.
U.S. Non-final Rejection for U.S. Appl. No. 14/343,504 dated Jun. 16, 2016.

* cited by examiner

PHARMACEUTICAL INJECTION SYSTEM

TECHNICAL FIELD

The present invention relates to a pharmaceutical injection system.

BACKGROUND ART

A conventional pharmaceutical injection system of this type was configured as follows.

Specifically, a conventional pharmaceutical injection system comprised a pharmaceutical injection device and a charging device in which this pharmaceutical injection device was placed. The pharmaceutical injection device had a main body case and a pharmaceutical syringe mounting portion that was provided within the main body case and to which a pharmaceutical syringe was removably mounted. The charging device further had a charger for charging the pharmaceutical injection device (see Patent Literature 1, for example).

CITATION LIST

Patent Literature

Patent Literature 1: International Laid-Open Patent Application 2006/059597

SUMMARY

With the conventional pharmaceutical injection device discussed above, the pharmaceutical contained in the pharmaceutical syringe is sometimes not injected all at once, but is instead divided up into a plurality of injections of a specific amount.

In this case, when one injection is finished, the pharmaceutical syringe that has been removed from the pharmaceutical syringe mounting portion is stored in a refrigerator or the like.

A problem here is that the user forgets to remove the pharmaceutical syringe, it can become heated, which may adversely affect the pharmaceutical contained inside it.

Specifically, when a single pharmaceutical injection is finished, the pharmaceutical injection device is placed in a charging device for charging. Accordingly, the pharmaceutical syringe would be heated by the heat generated during charging, and this could result in degradation of the pharmaceutical.

In view of this, it is an object of the present invention to prevent degradation of the pharmaceutical contained in the pharmaceutical syringe.

To achieve the stated object, the present invention comprises a pharmaceutical injection device, a charging device, a detector, and an alarm section. The pharmaceutical injection device has a main body case and a pharmaceutical syringe mounting portion provided within the main body case and to which a pharmaceutical syringe is removably mounted. The pharmaceutical injection device is placed in the charging device, and the charging device has a charger for charging the pharmaceutical injection device. The detector is provided to the pharmaceutical injection device and/or the charging device and detects whether or not the pharmaceutical syringe has been mounted to the pharmaceutical syringe mounting portion. The alarm section is connected to the detector and emits an alarm when it is detected that the pharmaceutical syringe has been mounted onto the pharmaceutical syringe mounting portion.

Advantageous Effects

Because the present invention is configured as above, the pharmaceutical contained in a pharmaceutical syringe can be prevented from being degraded.

Specifically, with the present invention, the detector detects the mounting of the pharmaceutical syringe to the pharmaceutical syringe mounting portion, and an alarm can be emitted from the alarm section, and this keeps the user from forgetting to remove the pharmaceutical syringe. As a result, degradation of the pharmaceutical can be prevented.

DESCRIPTION OF EMBODIMENTS

Embodiments of the present will now be described through reference to the drawings.

Embodiment 1

Figure 1:
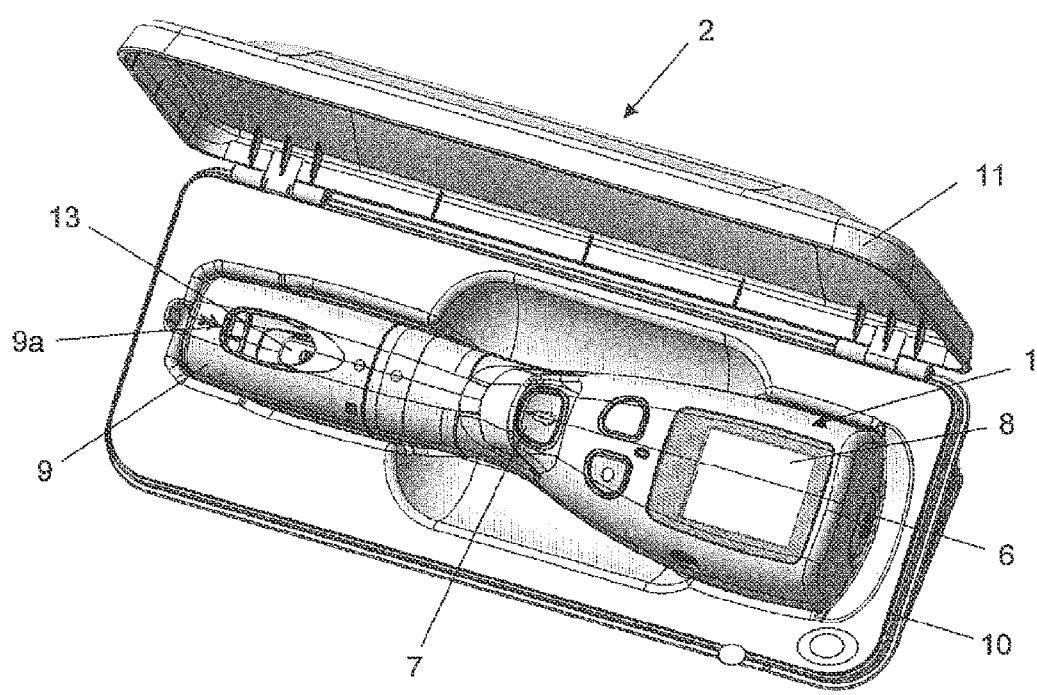
FIG. 1 is an oblique view of the configuration of the pharmaceutical injection system pertaining to Embodiment 1 of the present invention.

As shown in FIG. 1, the pharmaceutical injection device 1 in this embodiment is placed at a specific position on a charging device 2 during charging.

Figure 2:
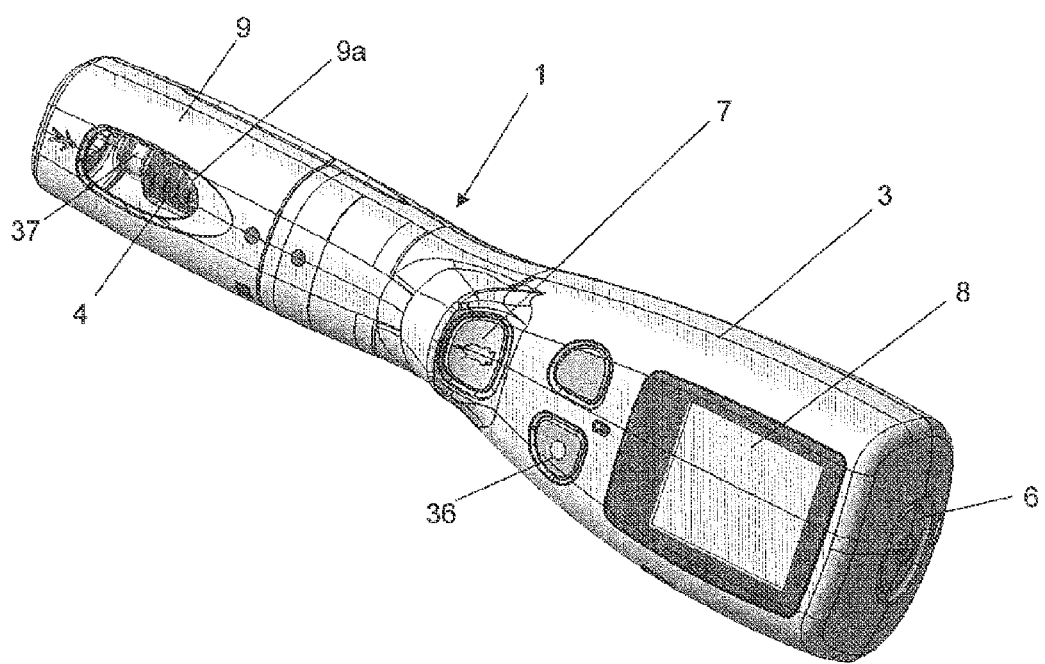
FIG. 2 is an oblique view of the pharmaceutical injection device included in the pharmaceutical injection system in FIG. 1.

As shown in FIG. 2, the pharmaceutical injection device 1 comprises a cylindrical main body case 3, a pharmaceutical syringe mounting portion 5 (see FIG. 4), a power button 6, a pharmaceutical injection button 7, a display section 8, and an air vent button 36.

The pharmaceutical syringe mounting portion 5 is provided within the main body case 3, and a pharmaceutical syringe 4 is removably mounted to the pharmaceutical syringe mounting portion 5. The pharmaceutical syringe mounting portion 5 has a distal end cap 9 mounted around its outer periphery.

The usual method for using the pharmaceutical injection device 1 will be briefly described.

First, as preparation, the pharmaceutical syringe 4 is mounted to the pharmaceutical syringe mounting portion 5 provided to the main body case 3 of the pharmaceutical injection device 1. Then, after an injection needle 37 (equipped with a needle cap) has been mounted to the pharmaceutical syringe 4, the distal end cap 9 is mounted to the distal end side of the main body case 3 (the side on which the pharmaceutical syringe and the injection needle are mounted). An upper face-side opening 9a and a lower face-side opening 9b are provided to the distal end cap 9.

Next, the power button 6 is switched on, and the pharmaceutical injection device 1 is started up.

After the pharmaceutical injection device 1 has been actuated, in this state in which the needle cap (not shown) of the mounted injection needle 37 is removed, and the distal end cap side of the pharmaceutical injection device 1 is faced upward, and the air vent button 36 is pressed. This discharges the air inside the pharmaceutical syringe 4 and the injection needle 37. Once this air venting is finished, the distal end cap 9 side is faced downward, and the opening side of the distal end cap 9 is pressed against the skin on the arm, abdomen, etc.

After this, the pharmaceutical injection button 7 provided on the outer peripheral face of the pharmaceutical injection device 1 is pressed, causing the injection needle 37 to pierce the skin automatically. This allows the pharmaceutical inside the pharmaceutical syringe 4 to be automatically injected in a specific amount into the body.

When the injection of a specific amount of pharmaceutical is finished, the injection operation is stopped automatically, and the injection needle inserted into the skin is also automatically retracted.

When the above pharmaceutical injection operation is complete, the pharmaceutical injection device 1 is moved away from the skin, and the needle cap is put back on the injection needle 37. The needle cap is removed from the pharmaceutical syringe 4 for every injection needle 37, and discarded at a specific site.

After this, the distal end cap 9 is removed, and the pharmaceutical syringe 4 mounted inside is removed from the pharmaceutical syringe mounting portion 5. If any pharmaceutical remains inside, the removed pharmaceutical syringe 4 is stored as it is in a refrigerator or the like.

Next, the power button 6 of the pharmaceutical injection device 1 is pressed to switch of the power to the pharmaceutical injection device 1.

The above procedure completes the series of steps involved in pharmaceutical injection with the pharmaceutical injection system in this embodiment.

Figure 3:
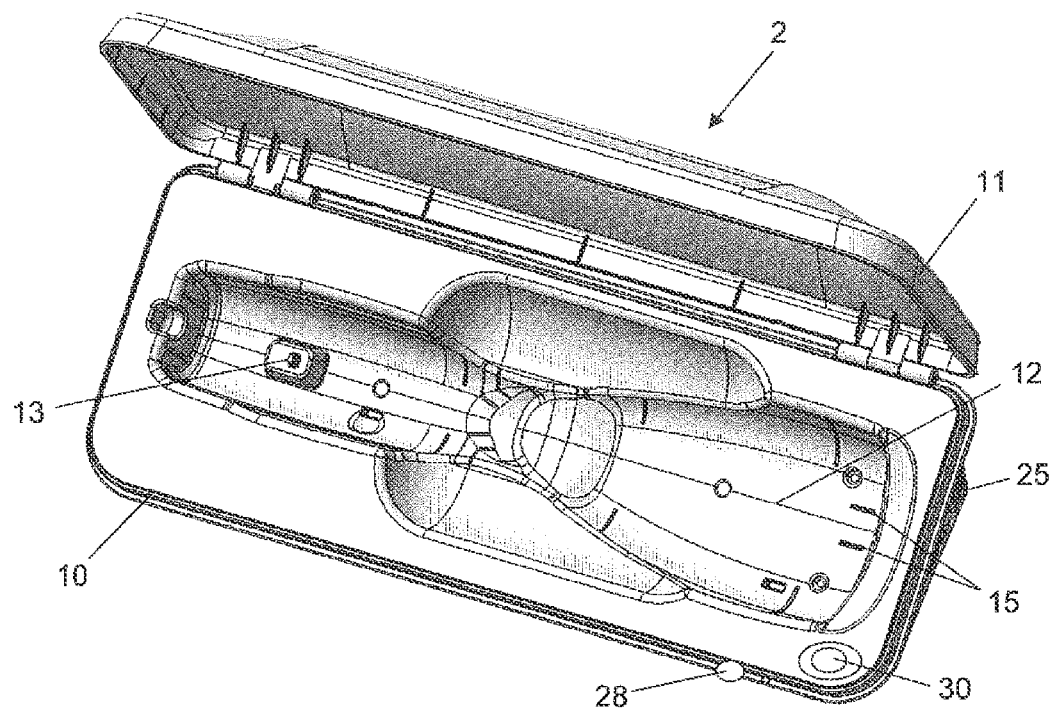
FIG. 3 is an oblique view of the charging device included in the pharmaceutical injection system in FIG. 1.

As shown in FIG. 3, the charging device 2 includes a lower case 10 and an upper case 11 that can be opened and closed. A recess 12 in which the pharmaceutical injection device 1 is placed during charging is formed in the lower case 10.

Figure 4:
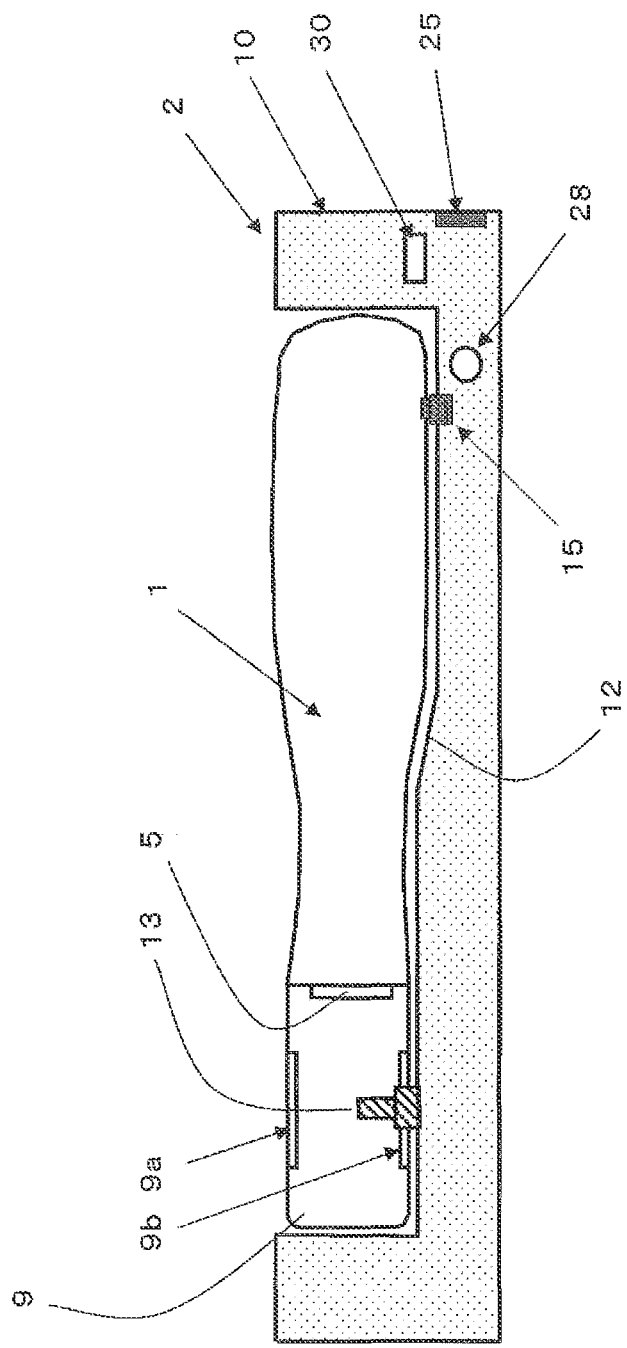
FIG. 4 is a cross section of the pharmaceutical injection system in FIG. 1.

As shown in FIG. 4, the charging device 2 has a detector 13 that is provided at the portion of the recess 12 corresponding to the distal end cap 9, and that detects whether or not the pharmaceutical syringe 4 has been mounted. Also, as shown in FIGS. 3 and 4, charging terminals 15 are provided at the portion of the recess 12 corresponding to charging terminals 14 of the pharmaceutical injection device 1 (see FIG. 6).

Figure 6:
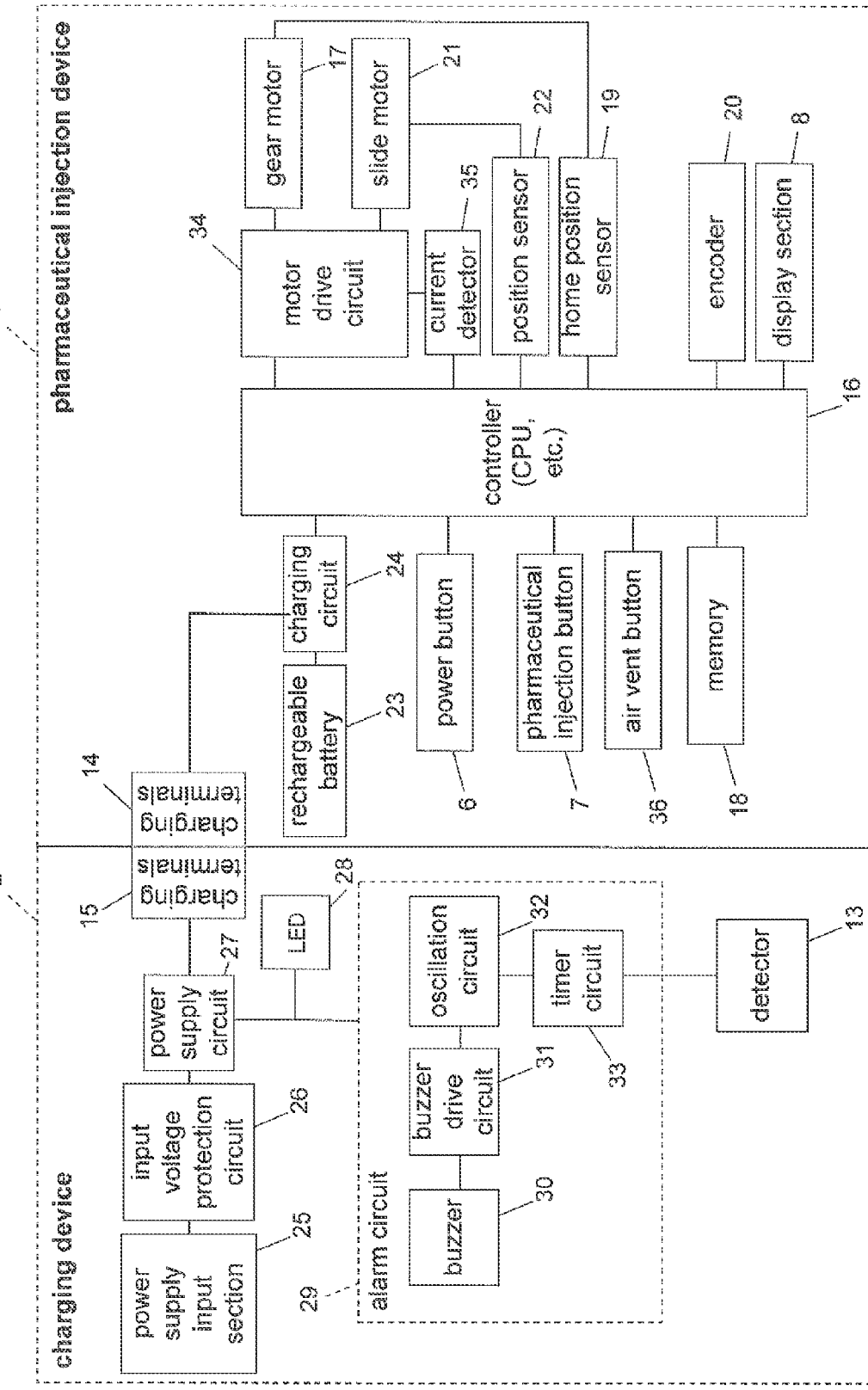
FIG. 6 is a block diagram of the electrical circuit of the pharmaceutical injection system in FIG. 1.

FIG. 6 shows the electrical control blocks of the pharmaceutical injection device 1 and the charging device 2.

The pharmaceutical injection device 1 has a controller 16. The controller 6 is connected to the power button 6, the pharmaceutical injection button 7, the air vent button 36, the display section 8, and so forth.

Since the configuration of the pharmaceutical injection device 1 is already well known, it will merely be described in brief through reference to FIG. 6. When a pharmaceutical is to be injected into the body, first the power button 6 is pressed, and then the pharmaceutical injection button 7 is pressed. A gear motor 17 is then driven by a motor drive circuit 34, and a piston (not shown) moves to the left in FIG. 2 (the distal end cap 9 side). As a result, a rubber presser (not shown) mounted on the pharmaceutical syringe 4 moves to the left, which causes a specific amount of the pharmaceutical contained in the pharmaceutical syringe 4 to be injected into the body.

The pharmaceutical injection device 1 in this embodiment is such that the pharmaceutical contained in the pharmaceutical syringe 4 is divided up into a plurality of injections. Thus, after every pharmaceutical injection, the pharmaceutical syringe 4 is removed from the pharmaceutical syringe mounting portion 5 and stored in a refrigerator or the like.

The amount of pharmaceutical injected is recorded to the memory 18 shown in FIG. 6, and the piston (not shown) pushes out a specific amount each time through the gear motor 17, according to this recorded information.

In this embodiment, however, the configuration is such that the piston returns to its home position after the pharmaceutical is injected. Thus, the home position of the piston is detected by a home position sensor 19.

Therefore, when the pharmaceutical is to be injected the next time, the piston (not shown) moves to the left in FIG. 2 by an amount equal to the sum of the amount of movement from the home position to the position at the completion of injection the last time, and the amount of injection movement the next time, according to the position at the completion of injection the last time recorded to the memory 18.

The amount of piston movement is sensed by an encoder 20. The actual injection of the pharmaceutical is performed by making the injection needle 37 mounted to the distal end of the pharmaceutical syringe 4 stick out from the distal end cap 9. This movement of the injection needle 37 is performed by a slide motor 21, and is monitored by a position sensor 22.

As shown in FIG. 6, the motor drive circuit 34 controls the gear motor 17 and the slide motor 21.

A current detector 35 monitors the current value during motor start-up, and notifies the motor drive circuit 34 if any sudden change in the current is detected during motor operation. This allows malfunction of the device to be detected and the operation to be halted.

The above configuration and operation are both well know, and therefore were only briefly described above, but the characteristic feature in this embodiment is that the pharmaceutical contained in the pharmaceutical syringe 4 is divided up into a plurality of injections, and after the injections, the pharmaceutical syringe 4 is removed from the pharmaceutical syringe mounting portion 5 every time and stored in a refrigerator or the like. This point will be described in detail below.

A rechargeable battery 23 is connected via a charging circuit 24 to the controller 16.

The rechargeable battery 23 also supplies power to other portions besides the controller 16, but these portions are not depicted in the drawings in order to keep the drawings from becoming too complicated.

The charging circuit 24 charges the rechargeable battery 23 with power inputted from the charging device 2 via the charging terminals 14 and 15.

The charging device 2 has a power supply input section 25. An input voltage protection circuit 26 and a power supply circuit 27 are connected between the power supply input section 25 and the charging terminals 15.

An LED 28 that indicates the supply of power, and an alarm circuit 29 are connected to the power supply circuit 27. The LED 28 is used to indicate that the pharmaceutical injection device 1 installed on the charging device 2 is being charged, and two or more may be provided.

The alarm circuit 29 has a buzzer 30 used as an alarm section, and a buzzer drive circuit 31 connected to this, an oscillation circuit 32, and a timer circuit 33.

The above-mentioned detector 13 is connected to the timer circuit 33.

In the above configuration, after the pharmaceutical is injected by the pharmaceutical injection device 1 shown in FIG. 2, the pharmaceutical injection device 1, whose pharmaceutical syringe 4 has been removed from the pharmaceutical syringe mounting portion 5, is placed in the recess 12 of the charging device 2 in order to charge the rechargeable battery 23, as shown in FIG. 4.

Figure 7:
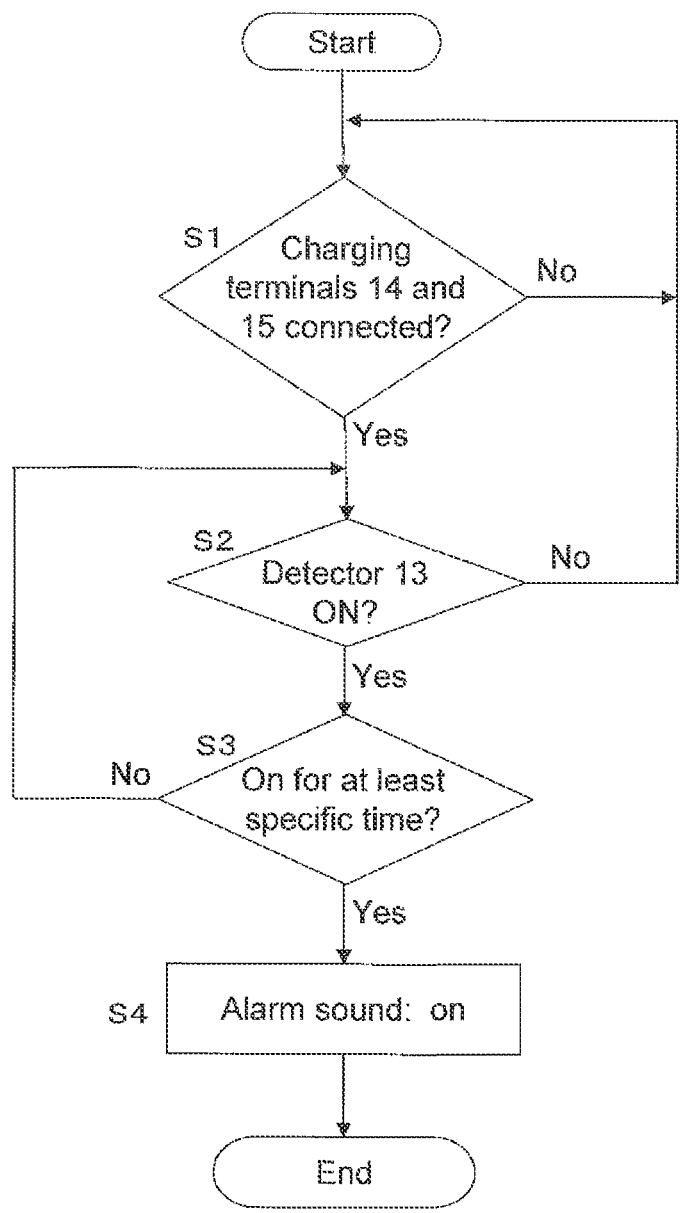
FIG. 7 is a flowchart of the operation of the pharmaceutical injection system in FIG. 1.

As shown in FIG. 6, the charging of the rechargeable battery 23 from the charging device 2 via the charging terminals 14 and 15 is begun in this state (S1 in FIG. 7).

When the pharmaceutical injection device 1 is thus placed on the charging device 2, the detector 13 senses whether or not the pharmaceutical syringe 4 is still on the pharmaceutical syringe mounting portion 5 of the pharmaceutical injection device 1 (S2 in FIG. 7).

Figure 5:
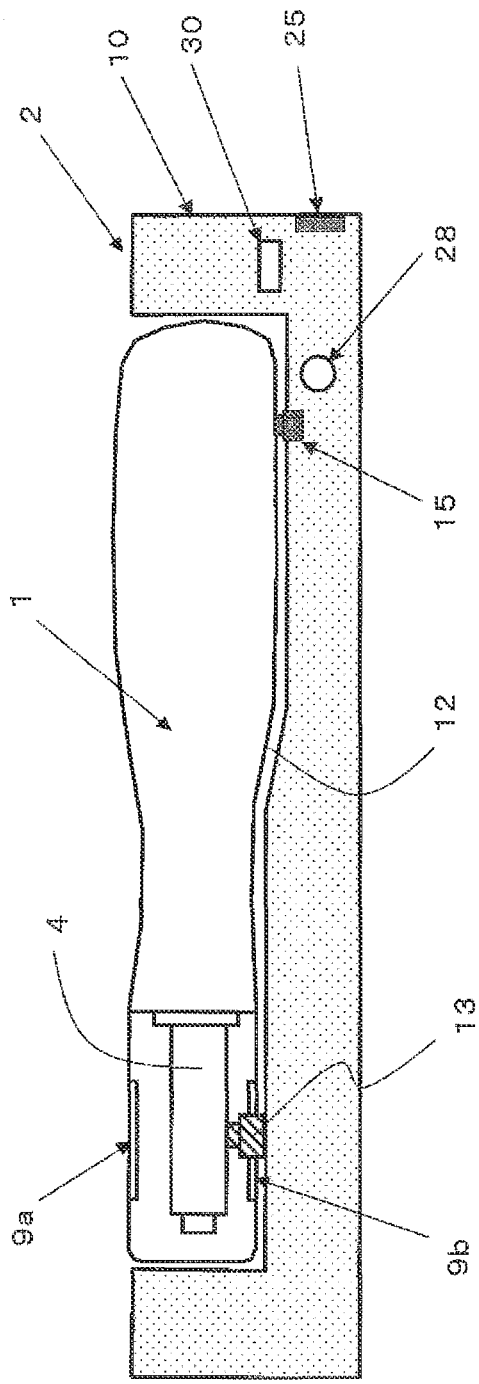
FIG. 5 is a cross section of the pharmaceutical injection system in FIG. 1.

Specifically, in this embodiment, after the injection of the pharmaceutical by the pharmaceutical injection device 1 shown in FIG. 2, the pharmaceutical syringe 4 need to be removed from the pharmaceutical syringe mounting portion 5 and stored in a refrigerator or the like. As shown in FIG. 5, however, if charging is performed in a state in which the pharmaceutical syringe 4 is still on the pharmaceutical syringe mounting portion 5, then the pharmaceutical remaining in the pharmaceutical syringe 4 will be heated by the heated generated by charging, and there is the risk that it will be degraded.

In view of this, in this embodiment, when this charging is begun, the detector 13 senses whether or not the pharmaceutical syringe 4 is still on the pharmaceutical syringe mounting portion 5.

More specifically, the distal end cap 9, which also serves as a protector, is provided to the outer periphery of the pharmaceutical syringe 4 mounted to the pharmaceutical syringe mounting portion 5. As show FIGS. 2, 4, and 5, the upper face-side opening 9a and lower face-side opening 9b are provided to the upper and lower face sides of the distal end cap 9.

The upper face-side opening 9a is mainly used to visually check whether or not the pharmaceutical syringe 4 is properly mounted to the pharmaceutical syringe mounting portion 5. The lower face-side opening 9b, meanwhile, is used not only to check the pharmaceutical syringe 4, but also as an opening into which the detector 13 is inserted, as shown in FIGS. 4 and 5.

That is, if the user forgets to remove the pharmaceutical syringe 4 and leaves the pharmaceutical syringe 4 attached to the pharmaceutical syringe mounting portion 5, then the detector 13 will be pushed by the pharmaceutical syringe 4, switching it on, as shown in FIG. 5.

This detector 13 is constituted by an on/off switch, and when it is switched on by being pressed by the pharmaceutical syringe 4, the timer circuit 33 is actuated. Once a specific length of time (such as one second) has elapsed (S3 in FIG. 7), the oscillation circuit 32, the buzzer drive circuit 31, and the buzzer 30 are actuated, and an alarm is sounded (S4 in FIG. 7).

The specific length of time (delay time) at the timer circuit 33 can be adjusted to a suitable value.

Therefore, this alarm reminds the user to remove the pharmaceutical injection device 1 from the recess 12 of the charging device 2, and to put the pharmaceutical injection device 1 back into the recess 12 after the pharmaceutical syringe 4 has been removed from the pharmaceutical syringe mounting portion 5.

In this state, as shown in FIG. 4, the pharmaceutical syringe 4 is not left on the pharmaceutical syringe mounting portion 5. Thus, the detector 13 is in its OFF state. Therefore, at this point no alarm is sounded from the buzzer 30, and charging of the rechargeable battery 23 continues in that state.

INDUSTRIAL APPLICABILITY

Since the present invention prevents the pharmaceutical injection device from being accidentally mounted to the charging device in a state in which the user has forgotten to take off the pharmaceutical syringe, degradation of the pharmaceutical contained in the pharmaceutical syringe can be prevented, which means that the present invention is particularly effective with a pharmaceutical injection system for administering a pharmaceutical that needs to be kept in a refrigerator or the like (such as a growth hormone).

REFERENCE SIGNS LIST 1 pharmaceutical injection device
2 charging device
3 main body case
4 pharmaceutical syringe
5 pharmaceutical syringe mounting portion
6 power button
7 pharmaceutical injection button
8 display section
9 distal end cap
9a upper face-side opening
9b lower face-side opening
10 lower case
11 upper case
12 recess
13 detector
14 charging terminal
15 charging terminal
16 controller
17 gear motor
18 memory
19 home position sensor
20 encoder
21 slide motor
22 position sensor
23 rechargeable battery
24 charging circuit
25 power supply input section
26 input voltage protection circuit
27 power supply circuit
28 LED
29 alarm circuit
30 buzzer
31 buzzer drive circuit
32 oscillation circuit
33 timer circuit
34 motor drive circuit
35 current detector
36 air vent button
37 injection needle

The invention claimed is:

1. A pharmaceutical injection system, comprising:
a pharmaceutical injection device that has a main body case, a rechargeable battery removably mounted in the main body case, and a pharmaceutical syringe mounting portion provided within the main body case and to which a pharmaceutical syringe is removably mounted;
a charging device in which the pharmaceutical injection device is placed, and which has a charger configured to charge the rechargeable battery in the pharmaceutical injection device;
a detector that is provided in or on the charging device and detects whether or not the pharmaceutical syringe has been mounted to the pharmaceutical syringe mounting portion; and
an alarm section that is connected to the detector, the alarm section being configured to emit an alarm when the detector detects that the pharmaceutical syringe has been mounted onto the pharmaceutical syringe mounting portion,
wherein the detector protrudes from the charging device to the pharmaceutical syringe mounting portion side of the pharmaceutical injection device, and includes a switch configured to be pressed by the pharmaceutical injection device when the pharmaceutical injection device has been placed in the charging device.

2. The pharmaceutical injection system according to claim 1, wherein the alarm section is provided in or on the charging device.

3. The pharmaceutical injection system according to claim 1, further comprising a timer circuit configured to set a delay time at which the alarm section is driven by the detector.

4. A pharmaceutical injection system, comprising:
a pharmaceutical injection device that has a main body case and a pharmaceutical syringe mounting portion provided within the main body case and to which a pharmaceutical syringe is removably mounted;
a charging device in which the pharmaceutical injection device is placed, and which has a charger configured to charge the pharmaceutical injection device;
a detector that is provided in or on the charging device and detects whether or not the pharmaceutical syringe has been mounted to the pharmaceutical syringe mounting portion; and
an alarm section that is connected to the detector, the alarm section being configured to emit an alarm when the detector detects that the pharmaceutical syringe has been mounted onto the pharmaceutical syringe mounting portion,
wherein the detector protrudes from the charging device to the pharmaceutical syringe mounting portion side of the pharmaceutical injection device, and includes a switch configured to be pressed by the pharmaceutical injection device when the pharmaceutical injection device has been placed in the charging device.

5. The pharmaceutical injection system according to claim 4, wherein the alarm section is provided in or on the charging device.

* * * * *